US010345280B2

(12) United States Patent
Sumption (10) Patent No.: US 10,345,280 B2
(45) Date of Patent: Jul. 9, 2019

(54) APPARATUS FOR MONITORING CONDITIONS WITHIN A WATER BODY (71) Applicant: GRAYDEN OUTDOOR, LLC, Brainerd, MN (US)

(72) Inventor: Trevor J. Sumption, Brainerd, MN (US)

(73) Assignee: GRAYDEN OUTDOOR LLC, Brainerd, MN (US)

( * ) Notice: Subject to any disclaimer, the term of this patent is extended or adjusted under 35 U.S.C. 154(b) by 198 days.

(21) Appl. No.: 15/490,891

(22) Filed: Apr. 18, 2017

(65) Prior Publication Data

US 2018/0302170 A1  Oct. 18, 2018

(51) Int. Cl.
*G01C 1/00* (2006.01)
*G01N 33/18* (2006.01)
*G01K 1/02* (2006.01)
*G01F 1/00* (2006.01)
*G01N 29/00* (2006.01)
*G01P 5/00* (2006.01)
*H04B 11/00* (2006.01)
(Continued)

(52) U.S. Cl.
CPC .......... *G01N 33/1886* (2013.01); *G01C 1/00* (2013.01); *G01F 1/002* (2013.01); *G01K 1/024* (2013.01); *G01N 29/00* (2013.01); *G01P 5/00* (2013.01); *H04B 11/00* (2013.01); *H04B 13/02* (2013.01); *G01K 2013/026* (2013.01)

(58) Field of Classification Search
CPC .......... H04B 11/00; G01F 1/00; G01F 1/002; G01K 1/02; G01K 1/024; G01N 33/18; G01N 33/1886
See application file for complete search history.

(56) References Cited

U.S. PATENT DOCUMENTS 7,062,878 B1 *  6/2006  Williams, Jr. ......... A01K 85/01
                                                      43/17.1
2003/0051390 A1 *  3/2003  Boys ..................... A01K 97/24
                                                      43/43.12

(Continued)

*Primary Examiner* — Isam A Alsomiri
*Assistant Examiner* — Amie M Ndure
(74) *Attorney, Agent, or Firm* — Cardle Patent Law CHTD (57) ABSTRACT A monitoring apparatus is disclosed herein. In various aspects, the monitoring apparatus includes a probe comprising a sensor to detect a condition within a water body, the sensor produces sensor data indicative of the condition within the water body. The probe includes a sound generator to propagates sound waves within the water body that communicate the sensor data from the probe, in various aspects. The monitoring apparatus includes an interface that is submersible within the water body, and the interface includes a receiver to receive the sound waves from the sound generator, in various aspects. A sleeve forms a portion of the interface and defines a sleeve passage, and a line passes slideably through the sleeve passage and is secured to the probe, in various aspects. The line cooperates with the interface and with the probe to orient the receiver and the sound generator with respect to one another to direct the sound waves from the sound generator to the receiver, in various aspects. This Abstract is presented to meet requirements of 37 C.F.R. § 1.72(b) only. This Abstract is not intended to identify key elements of the apparatus and methods disclosed herein or to delineate the scope thereof.

8 Claims, 4 Drawing Sheets (51) Int. Cl.
*H04B 13/02* (2006.01)
*G01K 13/02* (2006.01)

(56) References Cited

U.S. PATENT DOCUMENTS

| | | | | |
|---|---|---|---|---|
| 2006/0268664 A1* | 11/2006 | Lewis | ............... | A01K 79/02 |
| | | | | 367/139 |
| 2014/0022864 A1* | 1/2014 | Lebedev | ............. | G01S 7/003 |
| | | | | 367/107 |
| 2015/0085602 A1* | 3/2015 | Lebedev | ............. | G01S 15/96 |
| | | | | 367/3 |
| 2016/0245915 A1* | 8/2016 | Clark | ................. | G01S 15/96 |
| 2016/0341828 A1* | 11/2016 | Laster | ................ | G01S 15/96 |

* cited by examiner

APPARATUS FOR MONITORING CONDITIONS WITHIN A WATER BODY

BACKGROUND OF THE INVENTION

Field

The present disclosure relates to apparatus for the monitoring of temperature and/or other conditions in water bodies.

Background

Various conditions may exist throughout a body of water between the water surface and the bottom. Such conditions may include, for example, water temperature, turbidity, or water velocity at various depths. In a lake, for example, the temperature structure may be divided into three zones, the epilimnion, the thermocline, and the hypolimnion. The epilimnion, which is the strata of water generally proximate the water surface, generally has a warmer water temperature than the hypolimnion, which is a deeper strata of water within the water body. The thermocline is the transition between the epilimnion and the hypolimnion characterized by a water temperature gradient as the water temperature in the thermocline varies from the warmer water temperature of the epilimnion to the cooler water temperature of the hypolimnion. The water body may have other water temperature structures that may depend upon the season, the climate, and the nature of the water body. For example, rivers may have various temperature structures, and estuaries or the ocean may have various temperature structures. Lakes and reservoirs may experience a spring turnover or a fall turnover or both a spring turnover and a fall turnover during which temperature stratification disappears and the lake or reservoir is in a generally well-mixed condition. In addition, there may be currents within the water body, for example, due to inflows, outflows, or tides, and there may be different turbidities within the water body due to inflows, outflows, runoff that carry sediments into the water body.

Knowledge of the conditions within the water body may be important for fishermen. Certain species of fish may favor certain water temperatures or temperature structures. For example, fish may gather within the thermocline or proximate the boundary between the epilimnion and the thermocline. Some species of fish may prefer a current and other species may prefer stagnant waters. Certain species may prefer a particular turbidity such as clear or murky. The conditions preferred by a particular species of fish frequently have a limited range. Thus, in order to fish effectively for a certain species of fish, it may be important to locate the condition(s) in the water body preferred by the species being sought after.

Various probe devices have been developed to detect conditions within a water body. However, communication with the probe device may employ cables that extend to the probe at depth. Such cables may be expensive per unit length as well as awkward to use. Accordingly, there is a need for improved apparatus as well as related methods for monitoring conditions in water bodies.

BRIEF SUMMARY OF THE INVENTION

These and other needs and disadvantages may be overcome by the apparatus disclosed herein. Additional improvements and advantages may be recognized by those of ordinary skill in the art upon study of the present disclosure.

A monitoring apparatus is disclosed herein. In various aspects, the monitoring apparatus includes a probe comprising a sensor to detect a condition within a water body, the sensor produces sensor data indicative of the condition within the water body. The probe includes a sound generator to propagates sound waves within the water body that communicate the sensor data from the probe, in various aspects. The monitoring apparatus includes an interface that is submersible within the water body, and the interface includes a receiver to receive the sound waves from the sound generator, in various aspects. A sleeve forms a portion of the interface and defines a sleeve passage, and a line passes slideably through the sleeve passage and is secured to the probe, in various aspects. The line cooperates with the interface and with the probe to orient the receiver and the sound generator with respect to one another to direct the sound waves from the sound generator to the receiver, in various aspects.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

A monitoring apparatus that detects conditions within a water body is disclosed herein. In various aspects, the monitoring apparatus includes a probe, and the probe includes a sensor and a sound generator. With the probe lowered to a selected depth within the water body, the sensor may detect a condition within the water body, and the sensor may produce sensor data indicative of the condition. The sound generator propagates sound waves within the water body that communicate the sensor data from the probe to a receiver within an interface submerged within the water body, in various aspects. A line passes slidably through a sleeve passage of a sleeve that forms a portion of the interface and the line is secured to the probe, in various aspects. The line is tensioned to orient the receiver and the sound generator with respect to one another in order that the sound waves are directed from the sound generator within the probe to the receiver within the interface, in various aspects. The sound waves may form a cone and the line under tension positions the interface within the cone, in various aspects. The interface may then communicate the sensor data to a terminal by a cable that connects the terminal and interface to one another. The terminal may process the probe data for display to a user.

Figure 1:
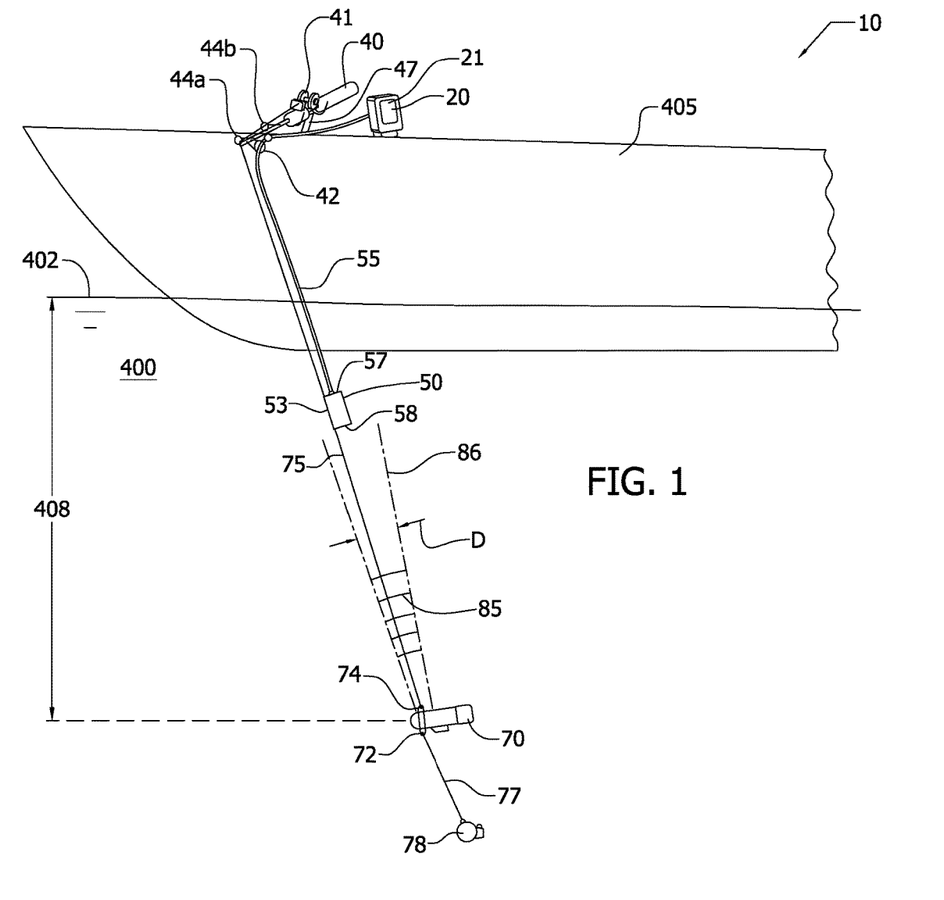
FIG. 1 illustrates by elevation view and exemplary implementation of a monitoring apparatus according to the present inventions.

FIG. 1 illustrates an implementation of monitoring apparatus 10. As illustrated in FIG. 1, monitoring apparatus 10 includes probe 70, probe rod 40, interface 50, and terminal 20. Probe 70, as illustrated, is submerged in water body 400 that may be, for example, a lake, reservoir, river, estuary, or the ocean. Line 75, which is attached to probe 70 at connector 74, passes slidably through sleeve passage 54 of sleeve 53 portion of interface 50 (also see FIG. 3B), through eyelets 44a, 44b, of probe rod 40, and line 75 is windingly received by reel 41 of probe rod 40, as illustrated. Accordingly, probe 70 may be lowered to or raised from depth 408 by unwinding line 75 from reel 41 or winding line 75 onto reel 41, respectively, and line 75 slides through sleeve passage 54 of sleeve 53 as probe 70 is lowered to or raised from depth 408.

Probe 70 is attached to line 77 at connector 72, in this implementation, and line 77 is attached to weight 78 that, for example, assists in submerging probe 70 to depth 408 in in water body 400. Connector 72, line 77, and weight 78 may be omitted as a separate element and incorporated into probe 70, in some implementations. Connectors 72, 74 may be formed, for example, as eyelets, holes, rings, links, clips, combinations thereof, as well as other attachment mechanisms disposed about probe 70. Various swivels, leaders, and so forth may be provided to attach lines 75, 77 to connectors 74, 72, respectively, in various implementations. Line 75 may be made of, for example, of polyamide (e.g. Nylon), polyvinylidene fluoride (PVDF) polyethylene, polyethylene terephthalate (e.g. Dacron) and ultra-high-molecular-weight polyethylene (e.g. Dyneema). Line 77 may be made of materials similar to that of line 75.

As illustrated in FIG. 1, interface 50 is attached to boat 405 by cable 55 and interface 50 may be submerged in water body 400 generally proximate water surface 402 of water body 400. In this implementation, cable 55, which is connected to interface 50, passes between interface 50 and terminal 20 through cable eyelet 42 of probe rod 40 to communicate sensor data 73 (see FIG. 5) between interface 50 and terminal 20. Cable 55 with interface 50 attached may be retracted or extended by hand to withdraw interface 50 from water body 400 or introduce interface 50 into water body 400, respectively, and cable 55 passes freely through cable eyelet 42 as cable 55 is retracted into boat 405 or extended forth from boat 405. In some implementations, cable 55 may be at least in part windingly received upon a spool (not shown) to allow cable 55 to be either extended or retracted. Cable 55 may be copper, optical fiber, or so forth as may be suitable for communication of signals 95, cable 55 may be sheathed for waterproofing or insulation, and cable 55 may be flexible.

Probe rod 40 is attached to boat 405 by rod holder 47, as illustrated in FIG. 1. Probe rod 40 may be removed from rod holder 47, for example, to allow the user to manipulate probe rod 40 as well as cable 55, line 75, interface 50, and probe 70 perhaps using, at least in part, probe rod 40. Certain implementations may omit cable eyelet 42, and cable 55 is manipulated without use of probe rod 40 in implementations that omit cable eyelet 42.

Figure 5:
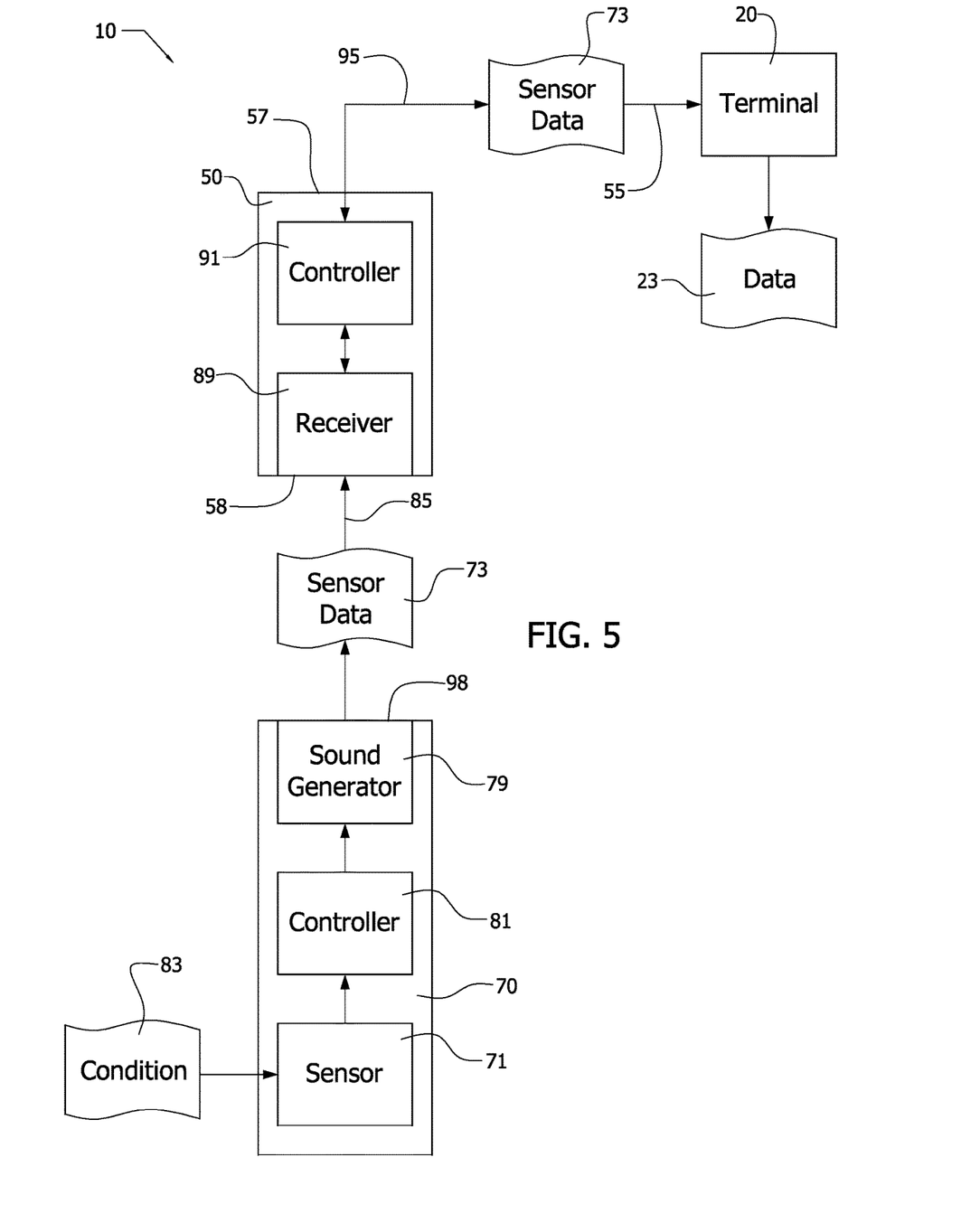
FIG. 5 illustrates by schematic view portions of the exemplary implementation of the monitoring apparatus of FIG. 1; and, FIG. 6A illustrates by elevation view the exemplary implementation of the monitoring apparatus of FIG. 1 in an exemplary operational position; and, FIG. 6B illustrates by elevation view the exemplary implementation of the monitoring apparatus of FIG. 1 in another exemplary operational position.

Probe 70 includes sensor 71 that produces sensor data 73 indicative of condition 83 detected by sensor 71 at depth 408, as illustrated in FIGS. 1 and 5. Condition 83 may include, for example, water temperature, depth, turbidity, water velocity, or combinations thereof as detected by sensor 71 at depth 408. Accordingly, sensor 71 may be formed as a thermocouple, pressure transducer, turbidity meter, velocity meter, or combination thereof. Sensor data 73, for example, may be a voltage or other analog measurement or a digital value (e.g. 8 bit, 16 bit, 32 bit) indicative of condition 83. Sensor 71 of probe 70 may collect sensor data 73, for example, as a single discrete measurement, as a periodic burst of measurements, or as a substantially continuous measurement.

As illustrated in FIG. 1, probe 70 generates sound waves 85 to communicate sensor data 73 from sensor 71 of probe 70 to interface 50. The sound waves 85 generated by probe 70, for example, may have a frequency of about 70 kHz, in some implementations. Sound waves 85 form cone 86 with diameter D, and diameter D of cone 86 increases as the sound waves 85 propagate away from probe 70, as illustrated in FIG. 1.

Interface 50, which is submerged within water body 400, receives sensor data 73 as sound waves 85 from probe 70, and interface 50 then communicates sensor data 73 to terminal 20 via cable 55 as signals 95, as illustrated in FIGS. 1 and 5. Interface 50 converts sound waves 85 into signals 95 that are transmitted, at least in part, over cable 55.

As illustrated in FIG. 1, line 75 is slidably received within sleeve passage 54 of sleeve 53, and line 75 is tensioned, at least in part, by weight 78 to orient end 58 of interface 50 toward probe 70 and position interface 50 within cone 86 to allow interface 50 to receive sensor data 73 from probe 70 as sound waves 85. Should interface 50 lie outside cone 86, probe 70 may be unable to communicate sensor data 73 to interface 50. By being under tension due to weight 78 (weight 78 may be external as in the illustrated implementation or internal within probe 70), line 75 cooperates with interface 50 and with probe 70 in this implementation to position interface 50 within cone 86 and to orient interface 50 and probe 70 with respect to one another to allow interface 50 to receive sound waves 85 from probe 70. Tension in line 75, as illustrated, positions the interface 50 within cone 86 so that the sound waves 85 are directed at interface 50 from probe 70. Tension in line 75, as illustrated, orients end 58 of interface 50 and surface portion 98 of probe 70 (see FIG. 3A) toward one another so that the sound waves 85 from surface portion 98 of probe 70 are directed at end 58 of interface 50.

Terminal 20 including display 21 is situated in boat 405, as illustrated in FIG. 1, to allow access by the user. While exemplary monitoring apparatus 10 is described herein in the context of boat 405, it should be recognized that exemplary monitoring apparatus 10 may be deployed in various other settings such as ice fishing, stationary structures such as bridges and piers, and buoys. Terminal 20 either alone or in combination with interface 50, in various implementations, processes sensor data 73, for example, to convert the sensor data 73 into data 23 having selected units (e.g. British or SI) and at selected depth(s), time(s), GPS location(s), and other such attributes. Terminal 20 may smooth sensor data 73 during conversion of sensor data 73 into data 23, and terminal 20 may, for example, remove outliers or eliminate noise from sensor data 73 during conversion of sensor data 73 into data 23. Terminal 20 may display data 23 on visual display 21 of terminal 20 to the user. Terminal 20 may accumulate data 23 and display the accumulation of data 23. For example, terminal 20 may display temperatures at a number of corresponding depths either graphically or in tabular form using display 21.

Figure 2:
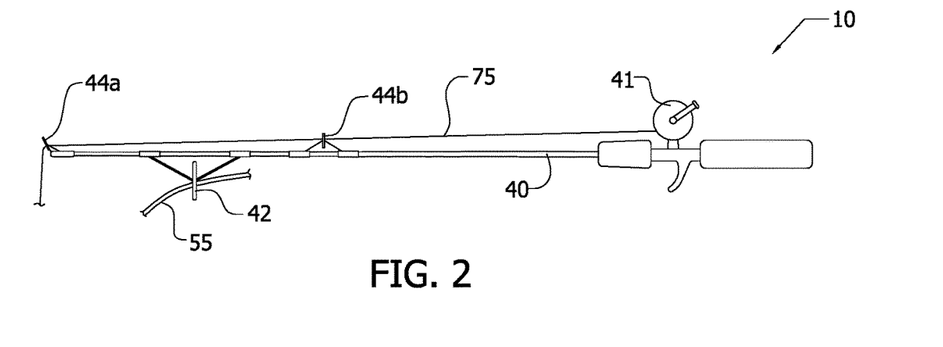
FIG. 2 illustrates by side view portions of the exemplary implementation of the monitoring apparatus of FIG. 1.

FIG. 2 illustrates probe rod 40 of exemplary monitoring apparatus 10. As illustrated in FIG. 2, line 75 passes through eyelets 44a, 44b of probe rod 40 and line 75 is windingly received by reel 41. Line 75 may be unwound from reel 41 or wound onto reel 41 in order to lower probe 70 into water body 400 or to withdraw probe 70 from water body 400, respectively. Probe rod 40 may include any number of eyelets, such as eyelets 44a, 44b, in various implementations. Reel 41 may be, for example, a barrel reel or spinning reel, in various implementations. Probe rod 40 includes cable eyelet 42, and cable 55 passes through cable eyelet 42, as illustrated, so that cable 55 is guided by cable eyelet 42 to be aligned with line 75 generally between probe rod 40 and interface 50. Cable eyelet 42 is sized to accommodate cable 55, and any number of cable eyelets, such as cable eyelet 42, may be located along probe rod 40, in various implementations.

Figures 3A, 3B, 4:
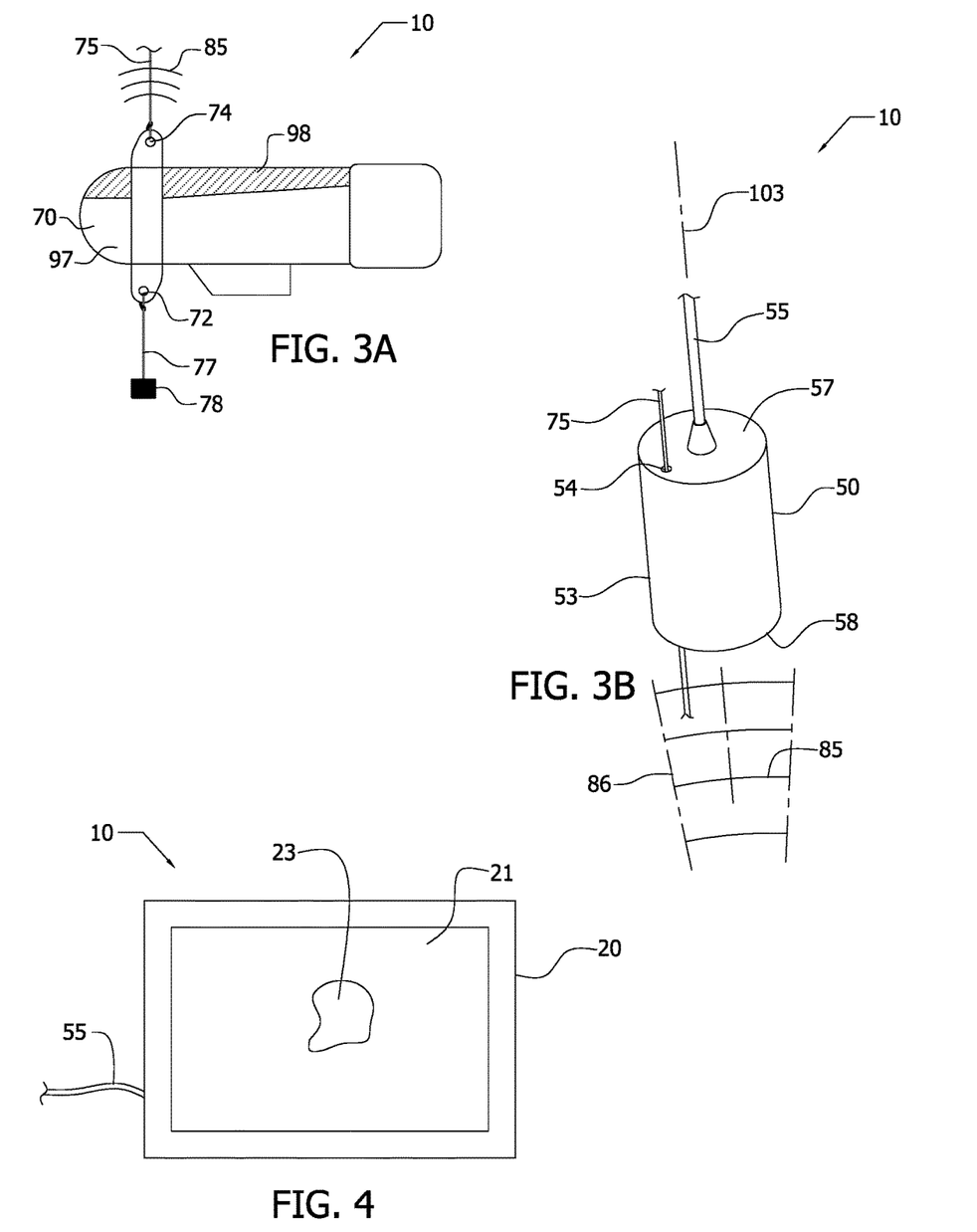
FIG. 3A illustrates by perspective view portions of the exemplary implementation of the monitoring apparatus of FIG. 1.
FIG. 3B illustrates by perspective view portions of the exemplary implementation of the monitoring apparatus of FIG. 1.
FIG. 4 illustrates by frontal view portions of the exemplary implementation of the monitoring apparatus of FIG. 1.

FIG. 3A illustrates probe 70 of exemplary monitoring apparatus 10. As illustrated in FIG. 3A, probe 70 has an elongated hydrodynamic shape with connectors 74, 72 to which lines 75, 77, respectively, may be attached. Probe 70, as illustrated, defines probe surface 97. Sound generator 79 (see FIG. 5) may be located within probe 70 to broadcast sound waves 85 from surface portion 98 of probe surface 97 of probe 70, and surface portion 98 is oriented toward interface 50. As illustrated in FIG. 3A, surface portion 98 of probe surface 97 is shown as shaded, and surface portion 98 generally includes portions of probe surface 97 including connector 74.

FIG. 3B illustrates interface 50 of exemplary monitoring apparatus 10. As illustrated in FIG. 3B, interface 50 has a cylindrical shape about axis 103 and with ends 57, 58 that are planar in this implementation. Ends 57, 58 may be rounded, bubbled out, or otherwise configured, in other implementations. Cable 55 is connected centrally to end 57, in this implementation. Sleeve 53, which defines sleeve passage 54, is oriented axially along interface 50 generally parallel to axis 103, and sleeve passage 54 generally passes between ends 57, 58, as illustrated. Sleeve 53 receives line 75, which is under tension between reel 41 and probe 70 due to weight 78, within sleeve passage 54 causing axis 103 to align generally parallel to line 75 and orienting end 58 of interface 50 towards surface portion 98 of probe 70. Because line 75 is drawn taut by weight 78, sleeve 53 is oriented parallel to line 75 by line 75 being received in sleeve passage 54, as illustrated in the Figures.

As illustrated in FIG. 5, receiver 89 is located within interface 50 in cooperation with end 58 to receive sound waves 85 from sound generator 79 within probe 70 when end 58 is oriented toward surface portion 98 of probe 70 by line 75 in sleeve passage 54. As illustrated in the various Figures, line 75 in sleeve passage 54 points axis 103 toward surface portion 98 of probe 70 and keeps interface 50 within cone 86 of sound waves 85.

FIG. 4 illustrates terminal 20 of monitoring apparatus 10. As illustrated in FIG. 4, terminal 20 cooperates with cable 55 so that terminal 20 is in data communication with interface 50 via cable 55. Terminal 20, as illustrated, includes display 21, and data 23 may be displayed upon display 21. Terminal 20 may include a microprocessor, memory, analogue to digital convertor, power source that powers terminal 20 and interface 50, and so forth, as would be readily understood by those of ordinary skill in the art upon study of this disclosure. In various implementations, terminal 20 may communicate with the Internet Cloud and, thence, to various devices in communication with the Internet Cloud to convert or to display data 23, and data 23 may include data, such as GPS data, that may be obtained via the Internet Cloud. Display 21 includes screens and other visual displays. In various implementations, terminal 20 may communicate, for example, via Bluetooth® or Wi-Fi with another device (not shown) that then interfaces with the internet. This device may be, for example, a mobile device (e.g. iphone) or one of a new generation of fish finder/chart plotter units, which are commonly referred to in the industry as Multi-Function Displays.

As illustrated in FIG. 5, probe 70 includes sensor 71, controller 81 and sound generator 79 enclosed within probe surface 97. Sensor 71 detects condition 83, as illustrated, and sensor 71 may cooperate with controller 81 to produce sensor data 73 indicative of condition 83. Portions of sensor 71 may communicate with probe surface 97 including water body 400 external to probe surface 97 to detect condition 83. Sensor data 73, in this implementation, is communicated from sensor 71 to controller 81 and thence to sound generator 79, and sound generator 79 generates sound waves 85 that propagate through water body 400 to communicate sensor data 73 from probe 70 to interface 50.

In this implementation, controller 81 cooperates with sensor 71 and with sound generator 79 to produce sensor data 73 and to control the generation of sound waves 85 by sound generator 79. Controller 81, for example, may include a microcontroller and power source, as would be readily recognized by those of ordinary skill in the art upon study of this disclosure. Note that sound generator 79 is place proximate surface portion 98 as indicated schematically in FIG. 5.

As illustrated in FIG. 5, interface 50 includes receiver 89 and controller 91. Sound waves 85 that communicate sensor data 73 from probe 70 to interface 50 are received by receiver 89, and sensor data 73 is communicated via cable 55 as signals 95 from interface 50 to terminal 20, as illustrated. Note that receiver 89 is place proximate end 58 of interface 50 as indicated schematically in FIG. 5.

Controller 91 cooperates with receiver 89 to control the reception of sound waves 85 by receiver 89 and to transform sound waves 85 into signals 95, in the implementation of FIG. 5. Controller 91 may include a microcontroller, A/D converter, and so forth, as would be readily recognized by those of ordinary skill in the art upon study of this disclosure. Terminal 20 converts sensor data 73 into data 23 that is displayed using display 21. In various implementations, terminal 20 may cooperate with interface 50 including controller 91 to convert sensor data 73 into data 23.

Figure 6A:
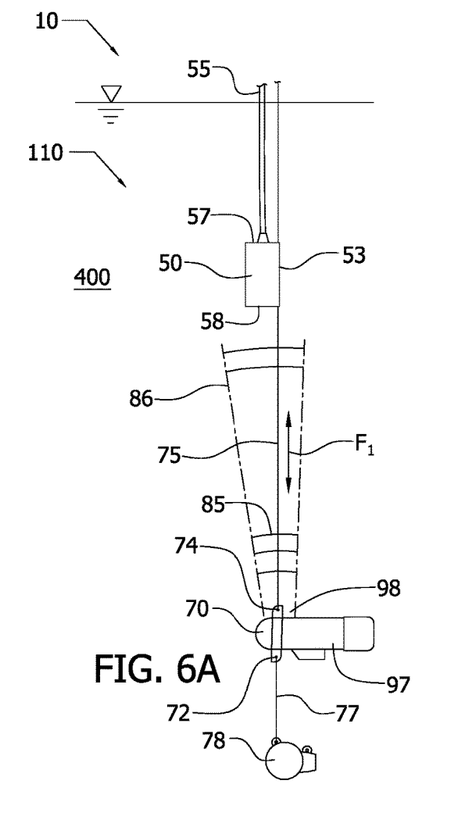
Figure 6B:
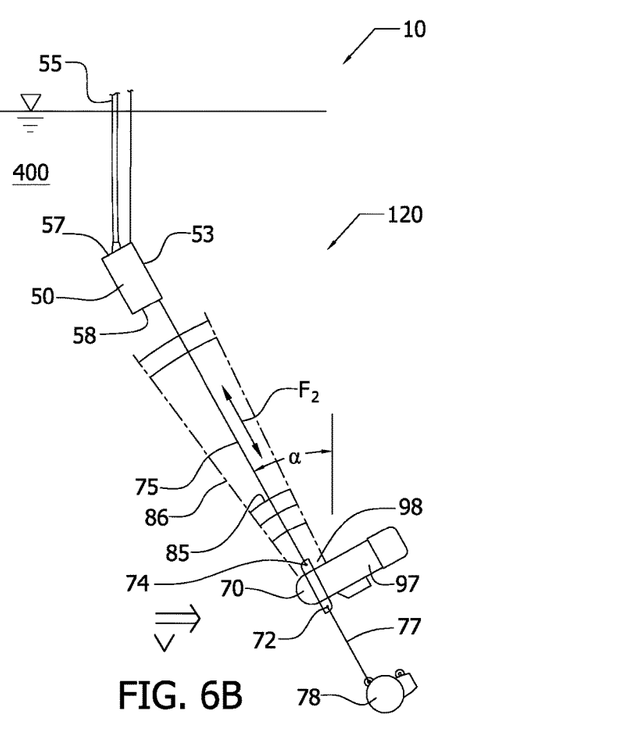

FIG. 6A illustrates monitoring apparatus 10 in exemplary operational position 110, and FIG. 6B illustrates monitoring apparatus 10 in exemplary operational position 120. As illustrated in FIGS. 6A & 6B, line 75 passes through sleeve passage 54 of sleeve 53 and line 75 is attached to probe 70. Weight 78 is attached to probe 70 by line 77, as illustrated. In operational position 110 illustrated in FIG. 6A, line 75 is tensioned to tensile force $F_1$ at least in part by weight 78, and line 75 under tension force $F_1$ cooperates with sleeve 53 and with probe 70 to orient end 58 of interface 50 and surface portion 98 of probe 70 toward one another. End 58 is faced toward surface portion 98, as illustrated in FIG. 6A. With end 58 and surface portion 98 oriented toward one another in operational position 110, sound waves 85 generated by sound generator 79 propagate from surface portion 98 of probe 70 to end 58 of interface 50 where sound waves 85 are received by receiver 89. Cone 86 of sound waves 85 is directed from probe 70 toward interface 50 and interface 50 is positioned within cone 86 by the tension force $F_1$ in line 75. Note that line 75 is generally vertical in exemplary operational position 110.

In operational position 120 illustrated in FIG. 6B, line 75 is tensioned to tensile force $F_2$ at least in part by a combination of weight 78 and drag force from water velocity V, which may be due to a current in water body 400. Line 75 is set at angle α with respect to the vertical in exemplary operational position 120. Line 75 under tension force $F_2$ cooperates with sleeve 53 and cooperates with probe 70 to orient end 58 of interface 50 and surface portion 98 of probe 70 toward one another. End 58 is faced toward surface portion 98, as illustrated in FIG. 6B. With end 58 and surface portion 98 oriented toward one another in operational position 120, sound waves 85 generated by sound generator 79 propagate from surface portion 98 of probe 70 to end 58 of interface 50 where sound waves 85 are received by receiver 89. In operational position 120, cone 86 of sound waves 85 is directed from probe 70 toward interface 50 and interface 50 is positioned within cone 86 by the tension force $F_2$ in line 75.

Thus, as illustrated in FIGS. 6A & 6B, various combinations of line 75, sleeve 53 of interface 50, line 77, weight 78 may comprise a positioning means cooperating with the interface 50 and with the probe 70 to position the interface 50 within cone 86 formed by sound waves 85 emanating from the sound generator 79. Sleeve 53 receives line 75, which is under tension between reel 41 and probe 70 due to weight 78, within sleeve passage 54, as illustrated. Sleeve 53 is then aligned parallel to line 75 by line 75 within sleeve passage 54 thus orienting end 58 of interface 50 towards surface portion 98 of probe 70.

In operation, the user may attach weight 78 to probe 70 by line 77, and the user may attach probe 70 to line 75 with line 75 passing slidably through sleeve passage 54 of sleeve 53. The user may connect cable 55 to terminal 20 and connect cable 55 to interface 50 with cable 55 passing through cable eyelet 42 of probe rod 40.

The user may place interface 50 into water body 400 with cable 55 connecting interface 50 with terminal 20, and the user may then lower probe 70 into water body to depth 408 by unwinding line 75 from reel 41 of probe rod 40. The user may select depth 408 by the selecting the length of line 75 unwound from reel 41. With probe 70 at depth 408, weigh 78 tensions line 75 thereby orienting end 58 of interface 50 and surface portion 98 of probe 70 toward one another and positioning interface 50 within cone 86. With end 58 and surface portion 98 oriented toward one another, sound waves 85 generated by sound generator 79 propagate from sound generator 79 through surface portion 98 of probe 70 to end 58 of interface 50 for reception by receiver 89.

Sensor 71 detects condition 83 and sensor 71 produces sensor data 73 indicative of condition 83 at depth 408. Sensor 71 may cooperate with controller 81 in detecting condition 83 or in producing sensor data 73. Sensor data 73 is then transmitted from probe 70 to receiver 89 by sound waves 85. Receiver 89 of interface 50 receives sound waves 85, and interface 50 transforms sound waves 85 into signals 95. Sensor data 73 is then communicated from interface 50 to terminal 20 as signals 95 via cable 55. Terminal 20 may convert sensor data 73 into data 23 and terminal 20 may display data 23 to the user using display 21. The user may traverse boat 405 about water body 400 to alter the location of probe 70 or the user may alter depth 408 of probe by winding or unwinding line 75 onto reel 41 or from reel 41, respectively, so that sensor data 73 may be obtained, for example, at a variety of depths, locations, or times. Data 23 may include sensor data 73 thus obtained at the variety of locations, depths and times.

When finished, the user may withdraw probe 70 from water body 400 by winding line 75 onto reel 41, and the user may withdraw interface 50 from water body 400 by pulling interface 50 out by cable 55 by hand. The user may then detach probe 70 from line 75 and the user may detach cable 55 from interface 50, from terminal 20, or from both interface 50 and terminal 20. Monitoring apparatus 10 including probe 70, interface 50, probe rod 40, cable 55, line 75, and terminal 20 may then be consolidated for storage.

The foregoing discussion along with the Figures discloses and describes various exemplary implementations. These implementations are not meant to limit the scope of coverage, but, instead, to assist in understanding the context of the language used in this specification and in the claims. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. A monitoring apparatus, comprising:
   a probe comprising a sensor to detect a condition within a water body, the sensor produces sensor data indicative of the condition, and the probe comprising a sound generator to propagates sound waves within the water body that communicate the sensor data from the probe;
   an interface submersible within the water body and comprising a receiver to receive the sound waves;
   a sleeve that forms a portion of the interface and defines a sleeve passage;
   a line that passes slideably through the sleeve passage and is secured to the probe, the line cooperates with the interface and with the probe to orient the receiver and the sound generator with respect to one another to direct the sound waves from the sound generator to the receiver.

2. The apparatus of claim 1, further comprising:
   a terminal in data communication with the interface by a cable to process the sensor data into data.

3. The apparatus of claim 2, further comprising:
   a display that cooperates with the terminal to display the data.

4. The apparatus of claim 1, further comprising;
a probe rod that cooperates with the line to position the probe within the water body, the probe rod further cooperates with a cable connected to the interface.

5. The apparatus of claim 4, the probe rod comprises and eyelet through which the line passes, a reel that windingly receives the line, and a cable eyelet through which the cable passes.

6. The apparatus of claim 1, wherein sensor data is indicative of one or more of temperature, velocity, and turbidity at a depth within the water body.

7. The apparatus of claim 1, further comprising;
a weigh secured to the probe to tension the line, at least in part.

8. A water monitoring apparatus, comprising:
a probe comprising a sensor and a sound generator, the sensor detects a condition within a water body and the sensor produces sensor data indicative of the condition, the sound generator propagates sound waves within the water body that communicate the sensor data from the probe;
an interface submersible within the water body and comprising a receiver to receive the sound waves;
a sleeve that forms a portion of the interface and defines a sleeve passage; and
positioning means cooperating slideably with the sleeve passage and with the interface and with the probe to position the interface within a cone formed by sound waves emanating from the sound generator.

\* \* \* \* \*